US011311192B1

(12) United States Patent
Allaka

(10) Patent No.: US 11,311,192 B1
(45) Date of Patent: Apr. 26, 2022

(54) METHODS AND SYSTEMS FOR PREDICTING PRINTED LABEL'S LIFE

(71) Applicant: Hand Held Products, Inc., Charlotte, NC (US)

(72) Inventor: Praveen Allaka, Charlotte, NC (US)

(73) Assignee: HAND HELD PRODUCTS, INC., Charlotte, NC (US)

( * ) Notice: Subject to any disclaimer, the term of this patent is extended or adjusted under 35 U.S.C. 154(b) by 0 days.

(21) Appl. No.: 17/090,224

(22) Filed: Nov. 5, 2020

(51) Int. Cl.
*A61B 5/00* (2006.01)
*G06K 9/62* (2022.01)
*G06K 7/14* (2006.01)

(52) U.S. Cl.
CPC .......... *A61B 5/0022* (2013.01); *A61B 5/6824* (2013.01); *A61B 5/7267* (2013.01); *G06K 7/1408* (2013.01); *G06K 7/1473* (2013.01); *G06K 9/6256* (2013.01)

(58) Field of Classification Search
CPC ... A61B 5/0022; A61B 5/6824; A61B 5/7267; G06K 7/1408; G06K 7/1473; G06K 9/6256
USPC ...................................... 340/573.1
See application file for complete search history.

(56) References Cited

U.S. PATENT DOCUMENTS

| 6,488,155 | B2 | 12/2002 | Lawandy et al. | |
|---|---|---|---|---|
| 9,189,842 | B2 * | 11/2015 | Liang | G06T 7/0008 |
| 2006/0267753 | A1 | 11/2006 | Hussey et al. | |
| 2010/0128296 | A1 * | 5/2010 | Denniston, Jr | G06F 3/03545 358/1.13 |
| 2014/0296755 | A1 | 10/2014 | Lack et al. | |
| 2017/0036471 | A1 * | 2/2017 | Biffert | B41J 3/01 |
| 2019/0087705 | A1 * | 3/2019 | Bourque | G06K 19/07762 |

FOREIGN PATENT DOCUMENTS

JP 2008-181475 A 8/2008

OTHER PUBLICATIONS

Rush, Alexandra. "The Life of Australian Banknotes", Bulletin, September Quarter 2015, pp. 55-62. Retrieved from https://www.rba.gov.au/publications/bulletin/2015/sep/7.html. Accessed Feb. 1, 2021.
Extended European search report dated Mar. 22, 2022 for EP Application No. 21205697, 10 pages.

* cited by examiner

*Primary Examiner* — Kerri L McNally
(74) *Attorney, Agent, or Firm* — Alston & Bird LLP

(57) ABSTRACT

Various embodiments illustrated herein disclose a method comprising receiving, by a processor, one or more patient characteristics associated with a first patient. The one or more patient characteristics comprises at least a type of sanitization, and/or a frequency of sanitization usage. Further, the method includes receiving one or more image characteristics associated with an image of a patient bracelet worn by the first patient. The method further includes training a machine learning (ML) model defining a relation between the one or more patient characteristics and the one or more image characteristics. The ML model is utilized to predict a count of days until the patient bracelet, associated with a second patient, deems unusable. Additionally, the method includes generating an instruction to a printing apparatus to print a new patient bracelet for the second patient based on the count of days being less than a predetermined number of days threshold.

20 Claims, 9 Drawing Sheets

METHODS AND SYSTEMS FOR PREDICTING PRINTED LABEL'S LIFE

TECHNICAL FIELD

Example embodiments of the present disclosure relate generally to a printed label and, more particularly, to systems and methods for predicting a printed label's life.

BACKGROUND

Generally, a printed label comprising printed machine readable indicia, fades over time. Fading of such labels deems the machine readable indicia unreadable, which may be desirable and may cause errors in tracking of an object/a human (when the machine readable indicia is utilized for tracking the object/human).

BRIEF SUMMARY

Various embodiments illustrated herein disclose a method comprising receiving, by a processor, one or more patient characteristics associated with a first patient, wherein the one or more patient characteristics comprises at least a type of sanitization, and/or a frequency of sanitization usage. The method further includes receiving, by the processor, one or more image characteristics associated with an image of a patient bracelet worn by the first patient. The method further includes training, by the processor, a machine learning (ML) model defining a relation between the one or more patient characteristics and the one or more image characteristics, wherein the ML model is utilized to predict a count of days until the patient bracelet, associated with a second patient, deems unusable. Additionally, the method includes generating, by the processor, an instruction to a printing apparatus to print a new patient bracelet for the second patient based on the count of days being less than a predetermined number of days threshold.

Various embodiments illustrated herein disclose a central server comprising a memory device storing one or more instructions. Further, the central comprises a processor communicatively coupled to the memory device, wherein the processor is configured to receive one or more patient characteristics associated with a first patient, wherein the one or more patient characteristics comprises at least a type of sanitization, and/or a frequency of sanitization usage. Additionally, the processor is configured to receive one or more image characteristics associated with an image of a patient bracelet worn by the first patient. Further, the processor is configured to train a machine learning (ML) model defining a relation between the one or more patient characteristics and the one or more image characteristics, wherein the ML model is utilized to predict a count of days until the patient bracelet, associated with a second patient, deems unusable. Furthermore, the processor is configured to generate an instruction to a printing apparatus to print a new patient bracelet for the second patient based on the count of days being less than a predetermined days threshold.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION OF THE INVENTION

Figure 1:
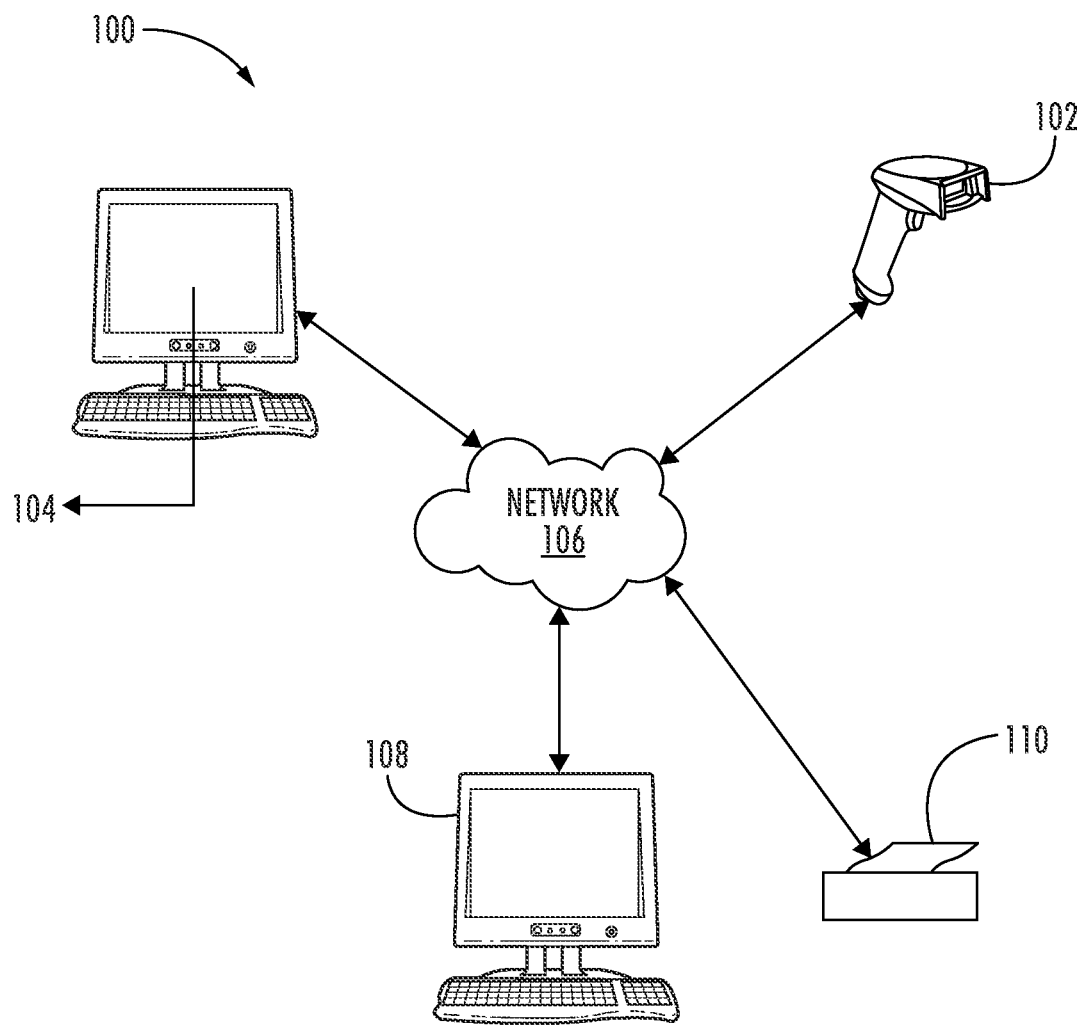
FIG. 1 illustrates a system environment where various embodiments of the present disclosure are implemented.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

Unless the context requires otherwise, throughout the specification and claims which follow, the word "comprise" and variations thereof, such as, "comprises" and "comprising" are to be construed in an open sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, one or more particular features, structures, or characteristics from one or more embodiments may be combined in any suitable manner in one or more other embodiments.

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly,"

"typically," "optionally," "for example," "often," or "might" (or other such language) be included or have a characteristic, that a specific component or feature is not required to be included or to have the characteristic. Such component or feature may be optionally included in some embodiments, or it may be excluded.

The term "electronically coupled," "electronically coupling," "electronically couple," "in communication with," "in electronic communication with," or "connected" in the present disclosure refers to two or more components being connected (directly or indirectly) through wired means (for example but not limited to, system bus, wired Ethernet) and/or wireless means (for example but not limited to, Wi-Fi, Bluetooth, ZigBee), such that data and/or information may be transmitted to and/or received from these components.

The term "indicium" has been broadly intended to include any indicia, or a machine readable code including Linear symbols, 2D barcodes (such as QR code, and Datamatrix codes), RFID tags, IR tags, near-field-communication (NFC) tags, and characters that are readable by a computing device (for example, an indicia scanner). Indicia are typically graphical representations of information (e.g., data), such as product numbers, package tracking numbers, patient barcode symbology identifier numbers, medication tracking identifiers, personnel barcode symbology identifier numbers, etc.

The term "quality" may refer to standard or protocol based on which content may be evaluated or compared with each other. For example, quality of an image may be evaluated based on sharpness of the image, noise in the image, dynamic range of the image, and/or the like. In some examples, the quality of the image may be further evaluated based on the quality of certain portions of the image. For example, the quality of the image may be evaluated based on quality of indicium in the image. To this end, the quality of the indicium may be evaluated based on ANSI X3.182, ISO15415, and ISO/IEC 15416 standards.

A typical printed label fades in due course of time. In some scenarios, where the printed label comprises a printed machine readable indicia, the machine readable indicia may fade in due course of time. Indicia scanner may not be able to scan and decode the faded machine readable indicia. Accordingly, tracking objects with such faded machine readable indicia may be error prone (since scanning and decoding of the faded machine readable indicia may be unsuccessful).

For example, the printed label (with the machine readable indicia) may correspond to a patient bracelet printed for one or more patients admitted to a hospital. Such patient bracelets are utilized for tracking the patients within the hospital premises. Additionally or alternatively, such patient bracelets are utilized to track a first set of patient characteristics. In some examples, the first set of patient characteristics includes, but not limited to, a type of disease associated with a patient, an age of the first patient, a name of the patient, a location of the patient within the hospital premises, a traversal history of the patient within the hospital premises, and/or the like. In scenarios, where the machine readable indicia on the patient bracelet fades, scanning and decoding of the machine readable indicia on the patient bracelet may fail, leading of errors monitoring of the patient.

Embodiments illustrated herein disclose systems and methods for predicting a life of a printed label. In an example embodiment, the printed label may correspond to a label or a medium on which a printer may print content. In some examples, the printed content may include a machine readable indicia. In an example embodiment, the machine readable indicia may be configured to store a first set of object characteristics pertaining to an object on which the printed label is attached. For example, in a hospital environment, the machine readable indicia is printed on a patient bracelet and is configured to store a first set of patient characteristics. In an example embodiment, the first set of patient characteristics may include, but not limited to, a name of the patient (on which the patient bracelet is attached), an age of the patient (on which the patient bracelet is attached), and a disease associated with the patient (on which the patient bracelet is attached). In some examples, the patient bracelet may facilitate monitoring of a location of the patient within the hospital premises. For example, when a patient is moved from one ward to another, the patient bracelet is scanned by an attendant of each ward, which allows monitoring of the patient's location within the hospital premises.

Additionally or alternately, the system includes an operator computing device that is configured to receive input from the attendant in the hospital pertaining to the patient. For example, the attendant may provide input to the operator computing device pertaining to a second set of patient characteristics associated with the patient. In an example embodiment, the second set of patient characteristics include, but are not limited to, a traversal history of the patient within the hospital, a type of sanitization used to disinfect the patient, a frequency of sanitization, and/or the like. In some examples, the first set of patient characteristics and the second set of patient characteristics may constitute the one or more patient characteristics. In some examples, the attendant may utilize the operator computing device to input both the first set of patient characteristics and the second set of patient characteristics. In response to inputting the one or more patient characteristics (i.e., the first set of patient characteristics and the second set of patient characteristics), the operator computing device may be configured to transmit the one or more patient characteristics to a central server.

In an example embodiment, the system further includes an indicia scanner that is configured to scan and decode the machine readable indicia, printed on the patient bracelet, to retrieve the first set of patient characteristics. Additionally or alternately, the indicia scanner may be configured to determine one or more image characteristics associated scanned image of the patient bracelet. The one or more image characteristics may include, but not limited to, a quality measure of the patient bracelet, information whether the decoding of the machine readable indicia is successful (hereinafter referred to as decode status). For example, the indicia scanner may be configured to determine the quality measure of the patient bracelet by determining the quality of the machine readable indicia (printed on the patient bracelet) based on ANSI X3.182, ISO15415, and ISO/IEC 15416 standards. In some examples, the decoding of the machine readable indicia may fail, as the machine readable indicia may have defects (such as but not limited to fading of the machine readable indicia). Additionally or alternatively, the indicia scanner may be configured to transmit the decode status to the central server. In some examples, the decode status may be indicative of the quality measure of the patient bracelet. For example, if the decoding of the machine readable indicia is successful, the decode status will indicate "successful". Accordingly, the quality of the patient bracelet is good. Similarly, if the decoding of the machine readable indicia is unsuccessful, the decode status will indicate "unsuccessful". Accordingly, the quality of the patient bracelet has degraded.

In an example embodiment, the central server may be configured to receive the one or more patient characteristics from the operator computing device (i.e., the second set of patient characteristics) and the indicia scanner (i.e., the first set of patient characteristics). Additionally or alternately, the central server may be configured to receive the one or more image characteristics from the indicia scanner. In some examples, the central server may be configured to generate a training data based on the one or more patient characteristics and the one or more image characteristics (associated with image scanned by the indicia scanner). In an example embodiment, the training data. In an example embodiment, the training data may include one or more features and one or more labels. The one or more features of the training data may include, but are not limited to, the first time period between successive scanning of the machine readable indicia, the current location of the patient within the hospital premises based on scanning of the machine readable indicia, a type of sanitizer historically used to disinfect the patient, a frequency of sanitizer usage, an age of the patient, the quality measure of the patient bracelet (received from indicia scanner), the decode status, and/or a disease associated with the patient. The one or more labels of the training data may include, but are not limited to, the count of days after which the patient bracelet had defects.

In an example embodiment, the central server may be further configured to train a machine learning (ML) model based on the training data. In an example embodiment, the ML model may define one or more relations and/or rules amongst the one or more features of the training data and the one or more labels of the training data. Thereafter, the central server may be configured to predict a second count of days until the patient bracelet is deemed unreadable or damaged. In some examples, the central server may transmit an instruction to print a new patient bracelet in a scenario where the second count of days is less than a predetermined threshold.

The disclosed embodiments encompass numerous advantages. For example, the disclosed embodiments allow to proactively determine a count of days until the patient bracelet is damaged. Accordingly, the central server may instruct the printer to proactively print the patient bracelet. To this end, the errors in monitoring of the patient (due to damaged patient bracelet) is avoided.

FIG. 1 illustrates a system environment 100 where various embodiments of the present disclosure are implemented. In an example embodiment, the system environment 100 may correspond to a hospital environment where one or more patients are treated for health related conditions. In an example embodiment, the system environment 100 includes an indicia scanner 102, an operator computing device 104, a network 106, a central server 108, and a printing apparatus 110.

In an example embodiment, the indicia scanner 102 may correspond to a mobile device, such as a hand-held indicia scanner, a portable data terminal, mobile phone, a tablet, portable computer, etc., or may be a stationary terminal being fixed to a single position, such as along an assembly line, which is capable of capturing the one or more images such as an image. In an example embodiment, the image may correspond to an image of a patient bracelet, which is worn by a first patient admitted in the hospital. In an example embodiment, the indicia scanner 102 may be capable of identifying and decoding a machine readable indicia in the image, to retrieve a first set of patient characteristics associated with the first patient, as is further described in conjunction with FIG. 5. Further, the indicia scanner 102 may be configured to determine one or more image characteristics associated with the image of the patient bracelet, as is further described in FIG. 5. The structure of the indicia scanner 102 is further described in conjunction with FIG. 4.

In an example embodiment, the operator computing device 104 may refer to a computing device that may be configured to provide an interface to an attendant in the system environment 100. For example, the operator computing device 104 may be configured to provide an interface for the nurses and/or doctors working in the hospital environment 100. In an example embodiment, through the interface, the attendant may input one or more patient characteristics associated with the first patient, as is further described in conjunction with FIG. 3. In an alternate embodiment, the attendant may be configured to input only a second set of patient characteristics (which is a subset of the one or more patient characteristics) associated with the first patient. Examples of the operator computing device 104 may include, but are not limited to, a personal computer, a laptop, a personal digital assistant (PDA), a mobile device, a tablet, or other such computing device. the structure of the operator computing device 104 is further described in conjunction with FIG. 2.

The network 106 corresponds to a medium through which content and messages flow between various devices in the system environment 100 (e.g., the central server 108, the operator computing device 104, and the indicia scanner 102). Examples of the network 106 may include, but are not limited to, a Wireless Fidelity (Wi-Fi) network, a Wireless Area Network (WAN), a Local Area Network (LAN), or a Metropolitan Area Network (MAN). Various devices in the system environment 100 can connect to the network 106 in accordance with various wired and wireless communication protocols such as, but not limited to, Transmission Control Protocol and Internet Protocol (TCP/IP), User Datagram Protocol (UDP), and 2G, 3G, 4G, or 5G communication protocols.

In an example embodiment, the central server 108 may refer to a computing device that may be configured to communicate with the indicia scanner 102 and the operator computing device 104. The central server 108 may comprise one or more processors and one or more memories. The one or more memories may include computer readable code that may be executable by the one or more processors to perform predetermined operations. Further, the central server 108 may include one or more interfaces that may facilitate communication with the indicia scanner 102 and the operator computing device 104, through the network 106. In an example embodiment, the central server 108 may be configured to receive the one or more image characteristics and the one or more patient characteristics from the indicia scanner 102 and the operator computing device 104, respectively. Further the central server 108 may be configured to generate training data, as is further described in FIG. 8. Additionally or alternatively, the central server 108 may be configured to train a ML model that is capable predicting a count of days until the patient bracelet fades, as is further described in FIG. 9. Examples of the central server 108 may include, but are not limited to, a personal computer, a laptop, a personal digital assistant (PDA), a mobile device, a tablet, or other such computing device. The structure of the central server 108 is further described in conjunction with FIG. 7.

In an example embodiment, the printing apparatus 110 may refer to an apparatus, such as copiers, printers, facsimile devices or other systems, may be capable of reproducing content, visual images, graphics, texts, etc. on a page or a media. Some examples of the printing systems may include, but not limited to, thermal printers, inkjet printers, laser printers, and/or the like. In an example embodiment, the printing apparatus 110 may receive an instruction from central server to print a patient bracelet.

In some examples, the scope of the disclosure is not limited to the system environment 100 having only one indicia scanner 102. In an example embodiment, the system environment 100 may have multiple indicia scanners that may be installed at multiple locations in the hospital premises. Similarly, the system environment 100 may include multiple operator computing devices.

Figure 2:
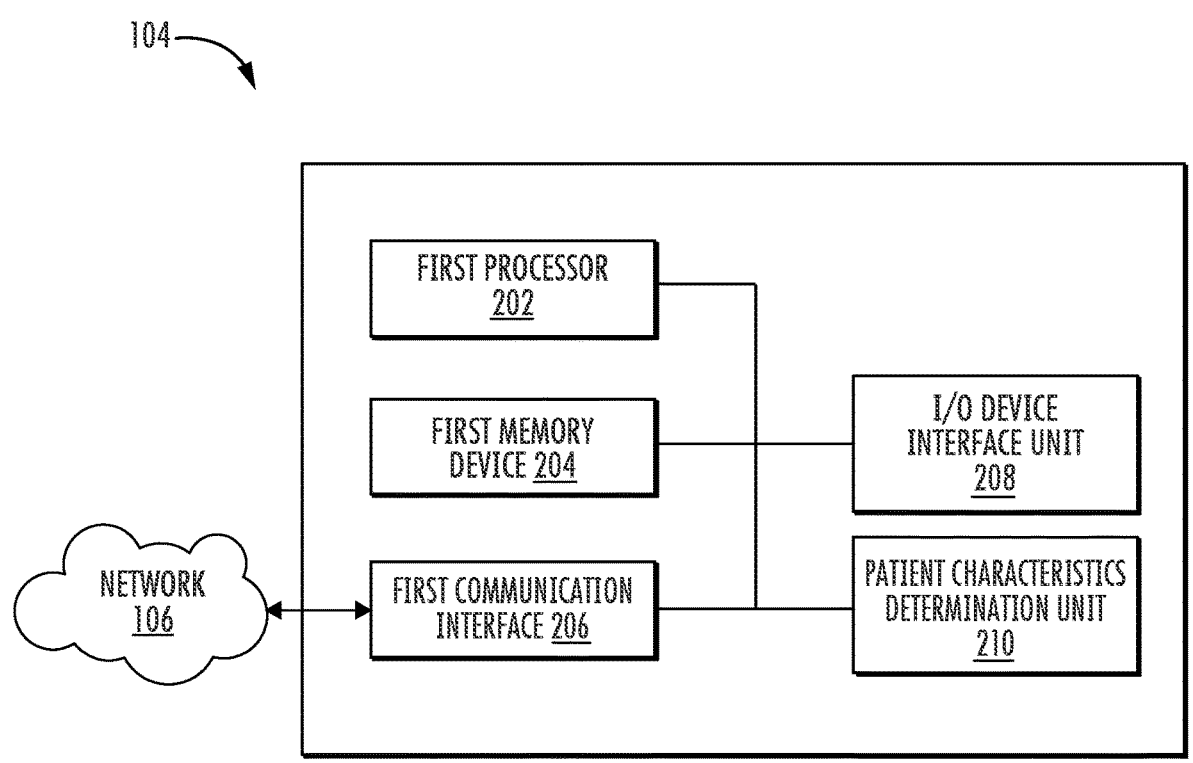
FIG. 2 illustrates a block diagram of an operator computing device, according to one or more embodiments described herein.
Figure 3:
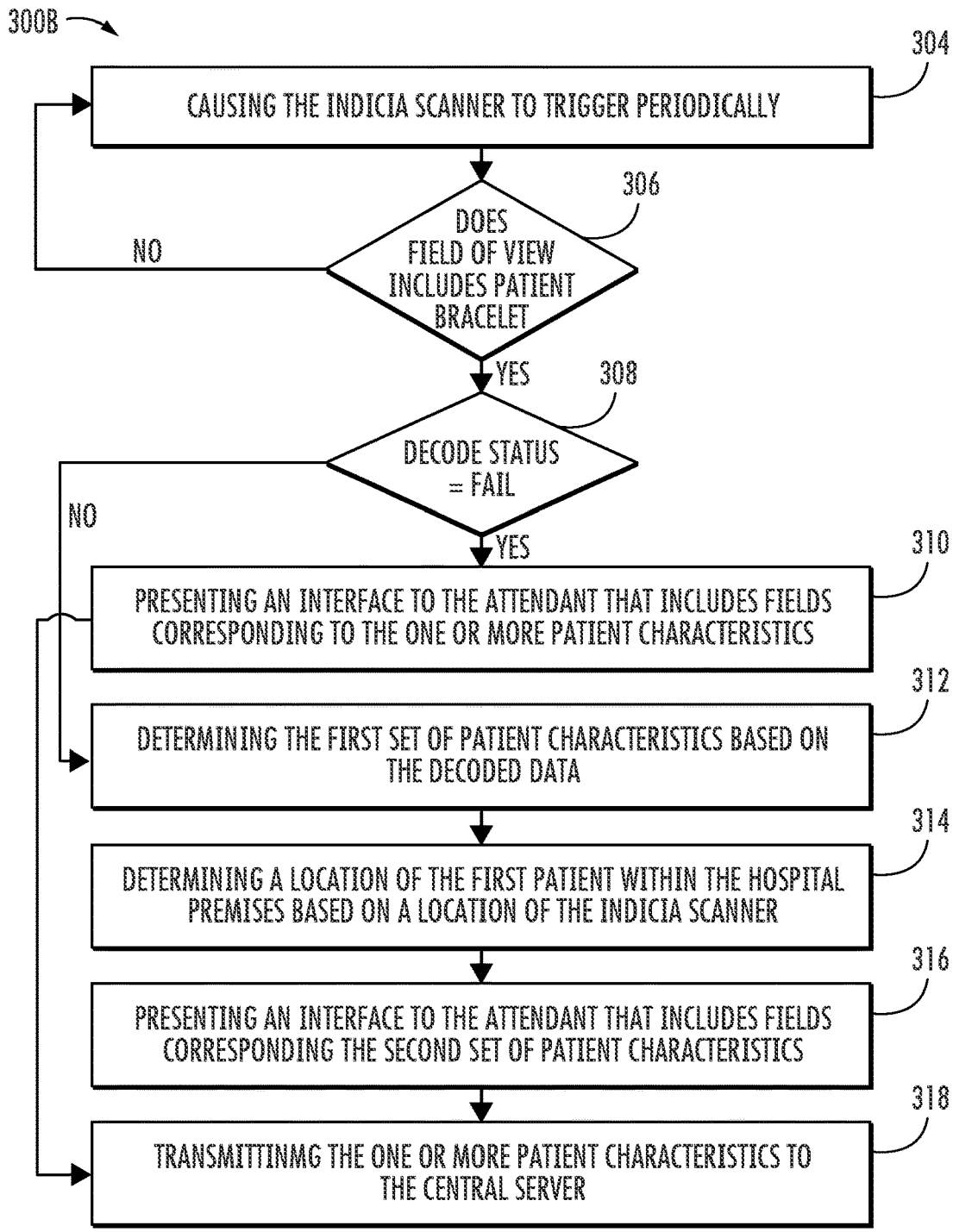
FIG. 3A illustrates a flowchart of a method for operating the operator computing device, according to one or more embodiments described herein.
FIG. 3B illustrates a flowchart of another method for operating the operator computing device, according to one or more embodiments described herein.

FIG. 2 illustrates a block diagram of the operator computing device 104, according to one or more embodiments described herein. The operator computing device 104 includes a first processor 202, a first memory device 204, a first communication interface 206, an Input/Output (I/O) device interface unit 208, and a patient characteristics determination unit 210.

The first processor 202 may be embodied as a means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC) or field programmable gate array (FPGA), or some combination thereof. Accordingly, although illustrated in FIG. 2 as a single processor, in an embodiment, the first processor 202 may include a plurality of processors and signal processing modules. The plurality of processors may be embodied on a single electronic device or may be distributed across a plurality of electronic devices collectively configured to function as the circuitry of the operator computing device 104. The plurality of processors may be in operative communication with each other and may be collectively configured to perform one or more functionalities of the circuitry of the operator computing device 104, as described herein. In an example embodiment, the first processor 202 may be configured to execute instructions stored in the first memory device 204 or otherwise accessible to the first processor 202. These instructions, when executed by the first processor 202, may cause the circuitry of the operator computing device 104 to perform one or more of the functionalities, as described herein.

Whether configured by hardware, firmware/software methods, or by a combination thereof, the first processor 202 may include an entity capable of performing operations according to embodiments of the present disclosure while configured accordingly. Thus, for example, when the first processor 202 is embodied as an ASIC, FPGA or the like, the first processor 202 may include specifically configured hardware for conducting one or more operations described herein. Alternatively, as another example, when the first processor 202 is embodied as an executor of instructions, such as may be stored in the first memory device 204, the instructions may specifically configure the first processor 202 to perform one or more algorithms and operations described herein.

Thus, the first processor 202 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor dedicated to running other applications. Software applications may be stored in the internal memory before they are accessed and loaded into the processors. The processors may include internal memory sufficient to store the application software instructions. In many devices, the internal memory may be a volatile or nonvolatile memory, such as flash memory, or a mixture of both. The memory can also be located internal to another computing resource (e.g., enabling computer readable instructions to be downloaded over the Internet or another wired or wireless connection).

The first memory device 204 may include suitable logic, circuitry, and/or interfaces that are adapted to store a set of instructions that is executable by the first processor 202 to perform predetermined operations. Some of the commonly known memory implementations include, but are not limited to, a hard disk, random access memory, cache memory, read only memory (ROM), erasable programmable read-only memory (EPROM) & electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an embodiment, the first memory device 204 may be integrated with the first processor 202 on a single chip, without departing from the scope of the disclosure.

Additionally or alternately, the first memory device 204 may be configured to store a mapping between the indicia scanner 102 and a location in the hospital premises where the indicia scanner 102 is installed. In an embodiment, where the system environment 100 includes multiple indicia scanner, the first memory device 204 may be configured to maintain a first look-up table that defines the mapping between the one or more locations in the hospital premises where the multiple indicia scanners 102 are installed. Following table 1 illustrates an example first look-up table:

TABLE 1 first look-up table illustrating mapping between the indicia scanner ID and the one or more locations.

| Indicia Scanner Identification (ID) | One or more locations |
|---|---|
| IS-1 | ICU |
| IS-2 | OPD |
| IS-3 | Orthopedic department |

The first communication interface 206 may correspond to a communication interface that may facilitate transmission and reception of messages and data to and from various devices operating in the system environment 100 through the network 106. For example, the first communication interface 206 is communicatively coupled with the central server 108 through the network 106. In some examples, through the first communication interface 206, the operator computing device 104 may be configured to transmit the one or more patient characteristics associated with a first patient to the central server 108. Examples of the first communication interface 206 may include, but are not limited to, an antenna, an Ethernet port, a USB port, a serial port, or any other port that can be adapted to receive and transmit data. The first communication interface 206 transmits and receives data and/or messages in accordance with the various communication protocols, such as but not limited to, I2C, TCP/IP, UDP, and 2G, 3G, 4G, or 5G communication protocols.

The I/O device interface unit 208 may include suitable logic and/or circuitry that may enable the operator computing device 104 to communicatively couple with one or more sensors. In an example embodiment, the one or more sensors may facilitate monitoring the traversal of the first patient within the hospital premises. Some examples of the one or more sensors may include, but not limited to, an image capturing device (such as the indicia scanner 102), a proximity sensor, and/or the like. In an example embodiment, the I/O device interface unit 208 may be configured to communicate with the one or more sensors using one or more known communication protocol such as I2C, Serial peripheral interface (SPI), and/or the like. For the purpose of ongoing description, the one or more sensors are considered to be indicia scanner 102 (a type of image capturing device) installed at predetermined locations within the hospital premises.

In some examples, the I/O device interface unit 208 may be further configured to present an interface to the attendant through a display device associated with the operator computing device 104. The interface may include an input form that may allow the attendant to input the one or more patient characteristics pertaining to the first patient. In an example embodiment, the one or more patient characteristics may include, but not limited to, a name of the first patient, an age of the first patient, a ward in which the first patient is staying, a traversal history of the patient, a type of sanitization used to disinfect the patient, a frequency of sanitization, and/or the like. In some examples, the scope of the disclosure is not limited to the attendant inputting the one or more patient characteristics. In an example embodiment, the operator computing device 104 may be configured to automatically determine a first set of patient characteristics of the one or more patient characteristics. In an example embodiment, the first set of patient characteristics may include, but not limited to, a name of the first patient, an age of the first patient, a disease of the first patient, a location of the first patient within the hospital premises and the traversal history of the first patient within the hospital premises. Further, in such an embodiment, the attendant may only have to input the second set of patient characteristics. In an example embodiment, the second set of patient characteristics may include, but not limited to, a type of sanitization used to disinfect the patient, a frequency of sanitization, and/or the like.

The patient characteristics determination unit 210 may include suitable logic and/or circuitry that may enable the operator computing device 104 to automatically determine the first set of patient characteristics. For example, the patient characteristics determination unit 210 may be configured to instruct the indicia scanner 102 to capture an image of the patient bracelet, while the patient traverses through the hospital premises. Thereafter, based on the location where the indicia scanner 102 is installed or positioned, the operator computing device 104 may be configured to determine the ward in which the first patient is staying, and the traversal history of the first patient within the hospital premises, as is further described in conjunction with FIG. 3. Additionally or alternately, the patient characteristics determination unit 210 may receive decoded data from the indicia scanner 102. In an example embodiment, the decoded data may include information pertaining to age of the first patient, name of the first patient, and a disease associated with the first patient. In an example embodiment, the patient characteristics determination unit 210 may consider the age of the first patient, the disease associated with the first patient, the location of the first patient, and the traversal history of the first patient, as the first set of patient characteristics. The patient characteristics determination unit 210 may be implemented one or more of Application Specific Integrated Circuit (ASIC) and Field Programmable Gate Array (FPGA).

The operation of the operator computing device 104 is further described in conjunction with FIG. 3A and FIG. 3B.

FIG. 3A illustrates a flowchart 300A of a method for operating the operator computing device 104, according to one or more embodiments described herein.

At step 302, the operator computing device 104 may include means such as the first processor 202, I/O device interface unit 208, and/or the like for presenting an interface on a display screen associated with the operator computing device 104. In an example embodiment, the interface may include a form that the attendant may fill in order to input the one or more patient characteristics. For example, the form may include one or more fields such as name of the first patient, age of the first patient, a ward in which the first patient is staying, a traversal history of the patient, a type of sanitization used to disinfect the patient, a frequency of sanitization, and/or the like.

In some examples, the scope of the disclosure is not limited to the operator computing device 104 receiving the input pertaining to the one or more patient characteristics associated with the first patient. In an example embodiment, the operator computing device 104 may be configured to automatically (i.e., without input from the attendant) determine the first set of patient characteristics of the one or more patient characteristics, associated with the first patient. The flowchart 300B explain the automatic determination of the first set of patient characteristics.

FIG. 3B illustrates a flowchart 300B of a method for operating the operator computing device 104, according to one or more embodiments described herein.

At step 304, the indicia scanner 102 may include means such as the first processor 202, I/O device interface unit 208, and/or the like for causing the indicia scanner 102 to trigger periodically. For example, the I/O device interface unit 208 may cause the indicia scanner 102 to trigger after 30 mins. Upon triggering the indicia scanner 102 may be configured to capture the image of the field of view. If the field of view includes the patient bracelet, the indicia scanner 102 may be configured to decode the machine readable indicia in the patient bracelet and may be configured to transmit the decoded data to the operator computing device 104. In an example embodiment, the decoded data includes information pertaining to name of the first patient, the age of the first patient, and disease associated with the first patient. Additionally or alternately, the indicia scanner 102 may be configured to transmit the decode status as "success" to the operator computing device 104. If the indicia scanner 102 fails to identify the patient bracelet within the field of view, the indicia scanner 102 may be configured to transmit information that "no patient bracelet identified in field of view" to the operator computing device 104. Additionally or alternately, if the indicia scanner 102 fails to decode the machine readable indicia in the patient bracelet (present in the field of view of the indicia scanner 102), the indicia scanner 102 may be configured to transmit the decode status as "fail" to the operator computing device 104.

At step 306, the operator computing device 104 may include means such as the first processor 202, the patient characteristics determination unit 210, and/or the like, for determining whether the patient bracelet is present in the field of view of the indicia scanner 102. For example, the operator computing device 104 may be configured to check for the reception of the information "no patient bracelet identified in field of view" from the indicia scanner 102. If the patient characteristics determination unit 210 determines that the operator computing device 104 has received the information "no patient bracelet identified in field of view", the patient characteristics determination unit 210 may be configured to repeat the step 304. However, if the patient characteristics determination unit 210 determines that the operator computing device 104 has not received the information "no patient bracelet identified in field of view", the patient characteristics determination unit 210 may be configured to perform the step 308.

At step 308, the operator computing device 104 may include means such as the first processor 202, the patient characteristics determination unit 210, and/or the like, for determining whether the decode status is "fail". If the patient characteristics determination unit 210 determines that the decode status is "fail", the patient characteristics determination unit 210 may configured to perform the step 310.

However, if the patient characteristics determination unit 210 determines that the operator computing device 104 has received the decoded data, the patient characteristics determination unit 210 may be configured to perform the step 312.

At step 310, the indicia scanner 102 may include means such as the first processor 202, the patient characteristics determination unit 210, the I/O device interface unit 208, and/or the like, for presenting an interface to the attendant that includes fields corresponding the one or more patient characteristics. Thereafter, the patient characteristics determination unit 210 may be configured to perform the step 318.

At step 312, the indicia scanner 102 may include means such as the first processor 202, the patient characteristics determination unit 210, the I/O device interface unit 208, and/or the like, for determining the first set of patient characteristics based on the decoded data. As discussed, the decoded data includes information pertaining to the name of the first patient, the age of the first patient, and disease associated with the first patient. In an example embodiment, the patient characteristics determination unit 210 may consider the name of the first patient, the age of the first patient, and disease associated with the first patient, as the first set of patient characteristics associated with the first patient.

Additionally or alternately, at step 314, the operator computing device 104 may include means such as the first processor 202, the patient characteristics determination unit 210, and/or the like, for determining a location of the first patient within the hospital premises based on a location of the indicia scanner 102 from which the operator computing device 104 received the decoded data. In an example embodiment, the patient characteristics determination unit 210 may refer to look-up table (table 1) to determine the location of the indicia scanner 102 in the hospital premises. In an example embodiment, the operator computing device 104 may be configured to consider the location of the indicia scanner 102 in the hospital premises as the location of the first patient in the hospital premises. As discussed in FIG. 1, the hospital premises may include more than one indicia scanner 102 that is installed at one or more locations within the hospital premises. The location of each of indicia scanner is stored in the look-up table in the operator computing device 104 along with the corresponding ID (e.g., table 1).

When the operator computing device 104 receives the decoded data from one of the indicia scanners, the operator computing device 104 may be configured to determine the location of the one of the indicia scanners from the look-up table. In an example embodiment, the patient characteristics determination unit 210 may be configured to add the location of the first patient in the first set of patient characteristics.

Additionally or alternately, the patient characteristics determination unit 210 may be further configured to determine traversal history of the first patient. In an example embodiment, the traversal history may correspond to list of locations where the first patient has visited within the hospital premises. In an example embodiment, the patient characteristics determination unit 210 may be configured to append the determined location of the first patient to the traversal history. Further, the patient characteristics determination unit 210 may be configured to add the traversal history of the first patient in the first set of patient characteristics.

At step 316, the indicia scanner 102 may include means such as the first processor 202, the patient characteristics determination unit 210, the I/O device interface unit 208, and/or the like, for presenting an interface to the attendant that includes fields corresponding the second set of patient characteristics. In an example embodiment, the second set of patient characteristics comprises, but not limited to, the type of sanitization used for disinfecting the first patient, and the frequency of sanitization. Thereafter, the patient characteristics determination unit 210 may be configured to perform the step 318.

In some examples, the patient characteristics determination unit 210 may determine the frequency of sanitization automatically. For example, the patient characteristics determination unit 210 may be configured to determine the frequency of the sanitization based on the traversal history. In such an embodiment, the patient characteristics determination unit 210 may utilize a hypothesis that the first patient may be sanitized every time the first patient is moved or traversed to a location. Accordingly, based on the traversal history of the first patient, the patient characteristics determination unit 210 may determine the frequency of sanitization. For instance, the first patient is moved between locations twice in three days. In such an embodiment, the patient characteristics determination unit 210 may determine the frequency of sanitation as 0.6 times per day. Additionally or alternately, the patient characteristics determination unit 210 may further consider a predetermined the count of times a patient is sanitized to determine the frequency of the sanitization. For example, the a predetermined the count of times a patient is sanitized in a day is 2 time per day. Accordingly, the frequency of the sanitization is 2.6 time per day.

At step 318, the operator computing device 104 may include means such as the first processor 202, the patient characteristics determination unit 210, and/or the like, for transmitting the one or more patient characteristics to the central server 108.

Figure 4:
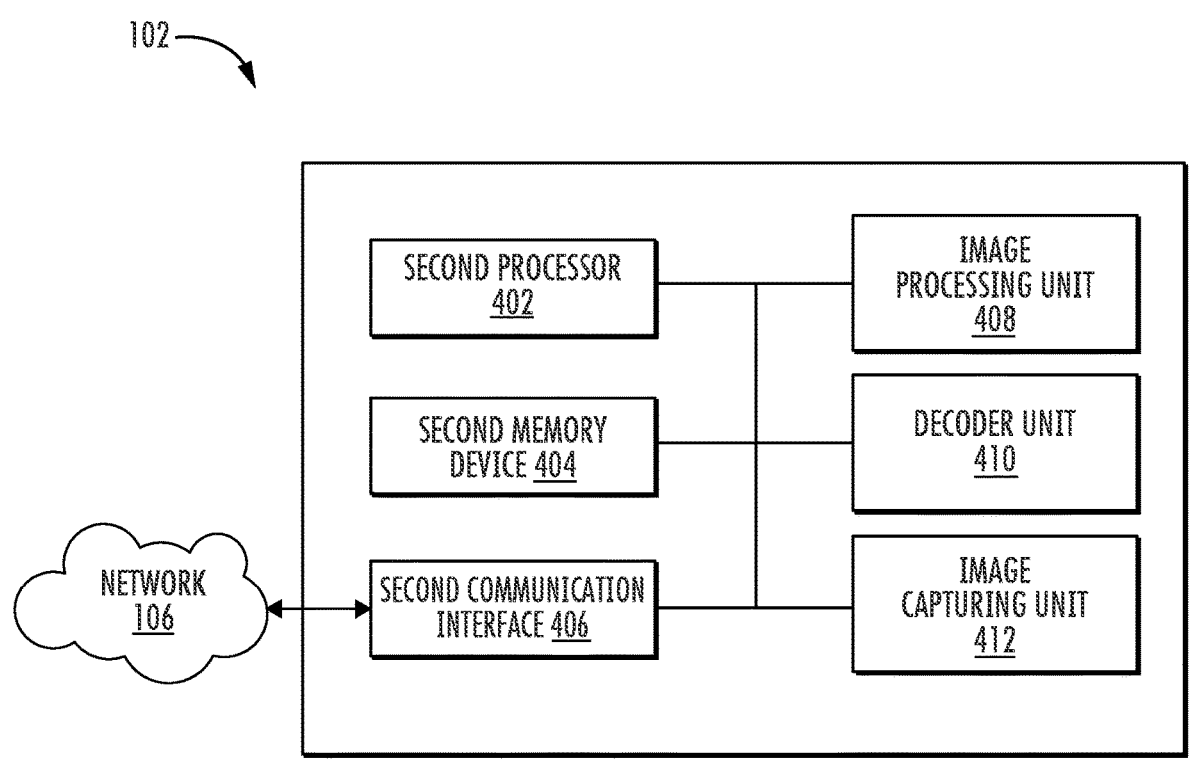
FIG. 4 illustrates a block diagram of an indicia scanner, according to one or more embodiments described herein.

FIG. 4 illustrates a block diagram of the indicia scanner 102, according to one or more embodiments described herein. In an example embodiment, the indicia scanner 102 may correspond to an image capturing device that is capable of capturing image of respective field of view. The indicia scanner 102 may include a second processor 402, a second memory device 404, a second communication interface 406, an image processing unit 408, a decoder unit 410, and an image capturing unit 412.

The second processor 402 may be embodied as a means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC) or field programmable gate array (FPGA), or some combination thereof. Accordingly, although illustrated in FIG. 4 as a single processor, in an embodiment, the second processor 402 may include a plurality of processors and signal processing modules. The plurality of processors may be embodied on a single electronic device or may be distributed across a plurality of electronic devices collectively configured to function as the circuitry of the indicia scanner 102. The plurality of processors may be in operative communication with each other and may be collectively configured to perform one or more functionalities of the circuitry of the indicia scanner 102, as described herein. In an example embodiment, the second processor 402 may be configured to execute instructions stored in the second memory device 404 or otherwise accessible to the second processor 402. These instructions, when executed by the second processor 402, may cause the circuitry of the indicia scanner 102 to perform one or more of the functionalities, as described herein.

Whether configured by hardware, firmware/software methods, or by a combination thereof, the second processor 402 may include an entity capable of performing operations according to embodiments of the present disclosure while configured accordingly. Thus, for example, when the second processor 402 is embodied as an ASIC, FPGA or the like, the second processor 402 may include specifically configured hardware for conducting one or more operations described herein. Alternatively, as another example, when the second processor 402 is embodied as an executor of instructions, such as may be stored in the first memory device 204, the instructions may specifically configure the second processor 402 to perform one or more algorithms and operations described herein.

Thus, the second processor 402 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor dedicated to running other applications. Software applications may be stored in the internal memory before they are accessed and loaded into the processors. The processors may include internal memory sufficient to store the application software instructions. In many devices, the internal memory may be a volatile or nonvolatile memory, such as flash memory, or a mixture of both. The memory can also be located internal to another computing resource (e.g., enabling computer readable instructions to be downloaded over the Internet or another wired or wireless connection).

The second memory device 404 may include suitable logic, circuitry, and/or interfaces that are adapted to store a set of instructions that is executable by the second processor 402 to perform predetermined operations. Some of the commonly known memory implementations include, but are not limited to, a hard disk, random access memory, cache memory, read only memory (ROM), erasable programmable read-only memory (EPROM) & electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an embodiment, the second memory device 404 may be integrated with the second processor 402 on a single chip, without departing from the scope of the disclosure.

The second communication interface 406 may correspond to a communication interface that may facilitate transmission and reception of messages and data to and from various devices operating in the system environment 100 through the network 106. For example, the second communication interface 406 is communicatively coupled with the central server 108 through the network 106. In some examples, through the second communication interface 406, the indicia scanner 102 may be configured to transmit the first set of patient characteristics associated with the first patient to the operator computing device 104. Further, the second communication interface 406 may be configured to transmit the one or more image characteristics to the central server 108. Examples of the second communication interface 406 may include, but are not limited to, an antenna, an Ethernet port, a USB port, a serial port, or any other port that can be adapted to receive and transmit data. The second communication interface 406 transmits and receives data and/or messages in accordance with the various communication protocols, such as but not limited to, I2C, TCP/IP, UDP, and 2G, 3G, 4G, or 5G communication protocols.

Figure 5:
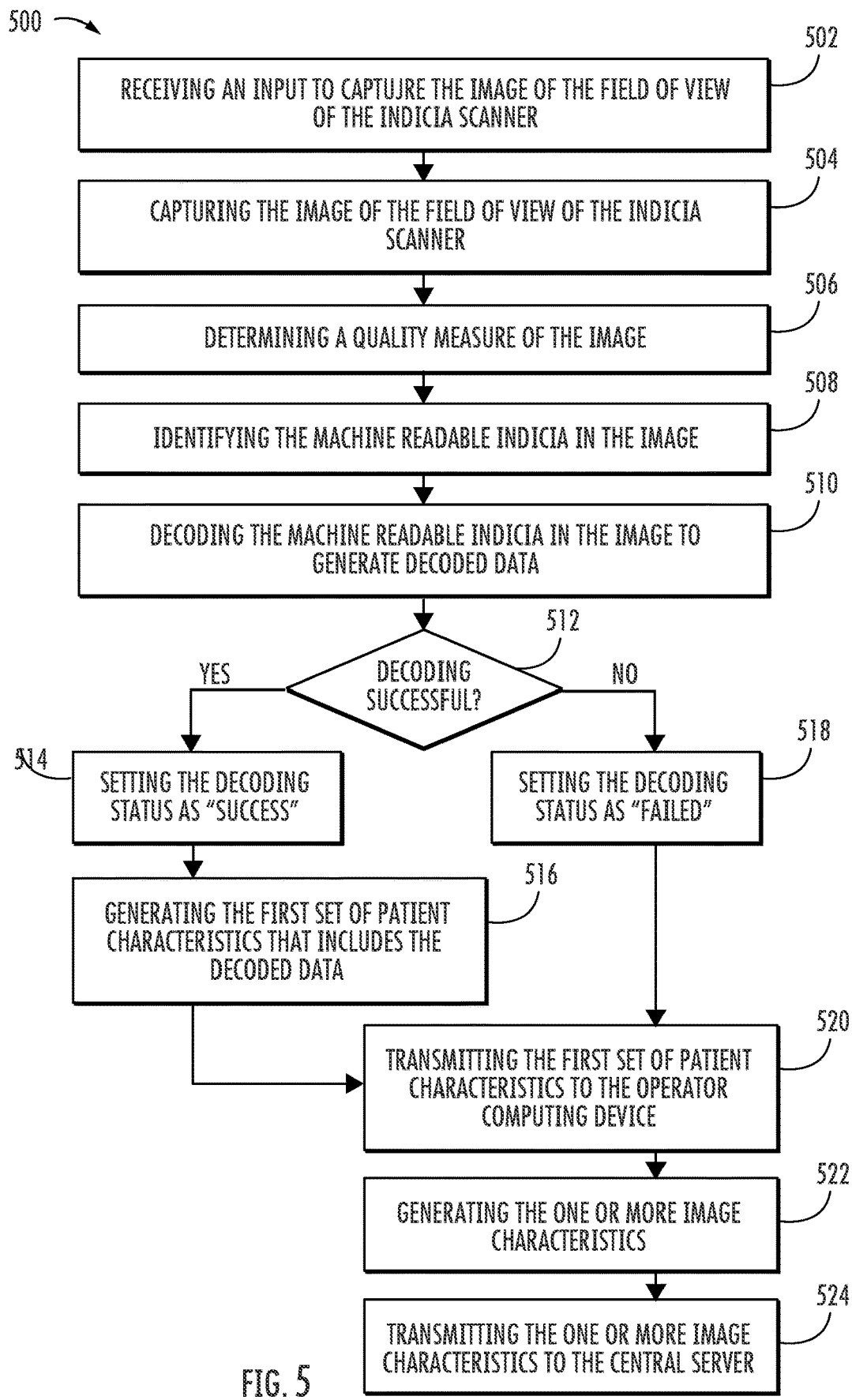
FIG. 5 illustrates a flowchart of a method for operating the indicia scanner, according to one or more embodiments described herein.

The image processing unit 408 may include suitable logic and/or circuitry that may enable the indicia scanner 102 to determine the quality measure of the image, as is further described in conjunction with FIG. 5. More particularly, the image processing unit 408 may be configured to compare the image with an ideal image to determine the quality measure of the image, as is further described in conjunction with FIG. 6. In another embodiment, the image processing unit 408 may be configured to determine the quality measure of the image based on the quality of the machine readable indicia in the image. In an example embodiment, the image processing unit 408 may be configured to determine the quality measure of the machine readable indicia based on one or more known quality standards such as ANSI X3.182, ISO15415, and ISO/IEC 15416 standards. Thereafter, the image processing unit 408 may be configured to consider the quality measure of the machine readable indicia as the quality measure of the image. The image processing unit 408 may be implemented using one or more of Application Specific Integrated Circuit (ASIC) and Field Programmable Gate Array (FPGA).

The decoder unit 410 may include suitable logic and/or circuitry that may enable the decoder unit 410 to identify the machine readable indicia in the image, as is further described in FIG. 5. Further, the decoder unit 410 may be configured to determine a barcode symbology identifier associated with the machine readable indicia, as is further described in conjunction with FIG. 5. In an example embodiment, the barcode symbology identifier of the machine readable indicia may be indicative of the type of the machine readable indicia. Some examples of the type of the machine readable indicia may include, but are not limited to, Code 39, Code 128, Code 11, PDF417, Datamatrix, QR Code, Aztec Code. In an example embodiment, the decoder unit 410 may be configured to decode the machine readable indicia in the image to generate decoded data. Additionally or alternately, the decoder unit 410 may be configured to determine the decode status, as is further described in FIG.

5. In an example embodiment, the decode status may correspond to a flag that is indicative of the successful decoding of the machine readable indicia in the image. The decoder unit 410 may be implemented using one or more of Application Specific Integrated Circuit (ASIC) and Field Programmable Gate Array (FPGA).

In an example embodiment, the image capturing unit 412 may include suitable logic and/or circuitry that may enable the image capturing unit 412 to capture an image of the field of view of the indicia scanner 102. In some examples, the image may include the image of the machine readable indicia. In an example embodiment, the image capturing unit 412 may include an image sensor. In some examples, the image sensor is referred to as a solid state device that is capable of generating electrical signals corresponding to the light signals that impinges on the image sensor. Some examples of the image sensor may include a color or monochrome 1D or 2D charged coupled device (CCD), complementary MOSFET (CMOS), Contact image sensor (CIS) or any other device, that may be capable to generate electrical signal based on the received light signals. In addition to the image sensor, the image capturing unit 412 may include one or more optical assemblies such as one or more lenses, one or more gratings, and/or one or more mirrors that may facilitate directing the light from the field of view on to the image sensor. Additionally or alternatively, the image capturing unit 412 may further include one or more driving units that may be capable of causing the one or more optical assemblies along a predetermined path. Such traversal of the one or more optical assemblies may enable focusing of the light onto the image sensor.

FIG. 5 illustrates a flowchart 500 of a method for operating the indicia scanner 102, according to one or more embodiments described herein.

At step 502, the indicia scanner 102 may include means such as the first processor 202, and/or the like, for receiving an input to capture the image of the field of view of the indicia scanner 102. In an example embodiment, the operator of the indicia scanner 102 may provide the input to the indicia scanner through a trigger button on the indicia scanner 102. For example, the operator may push the trigger button. In an example embodiment, in response to pushing the trigger button, the trigger button of the indicia scanner 102 may generate a trigger signal that is indicative of the received input from the operator. In some examples, the scope of the disclosure is not limited to the operator pressing the trigger button to provide the input of the indicia scanner 102. In an example embodiment, the indicia scanner 102 may trigger automatically as soon as the indicia scanner 102 detects an object present in the respective field of view. In another example, the indicia scanner 102 may receive the input from a remote computer such as an operator computing device 104 being operated by the attendant.

At step 504, the indicia scanner 102 may include means such as the second processor 402, the image capturing unit 412 and/or the like for capturing the image of the field of view of the indicia scanner 102. In some examples, the second processor 402 may cause the image capturing unit 412 to capture the image in response to the reception of the trigger signal from the trigger button. As discussed, the image capturing unit 412 may include the image sensor and the one or more optical assemblies that may direct the light from the field of view of the indicia scanner 102 onto the image sensor. Accordingly, the image sensor may generate electrical signals that are representative of the image. Additionally or alternatively, the second processor 402 may be configured to render the image based on the electrical signal received from the image sensor.

At step 506, the indicia scanner 102 may include means such as the second processor 402, the image processing unit 408, and/or the like, for determining a quality measure of the image. In some examples, the image processing unit 408 may be configured to compare the image with the ideal image to determine the quality measure of the image. In an example embodiment, the ideal image may correspond to an image of the patient bracelet, which is free from defects (e.g., smudges and/or fading). In some examples, the determination of the quality measure of the image is further described in conjunction with FIG. 6. In an example embodiment, the quality measure of the image is indicative of the quality measure of the patient bracelet.

In some examples, the scope of the disclosure is not limited to determining the quality measure of the patient bracelet based on the comparison of the image with the ideal image. In an example embodiment, the image processing unit 408 may be configured to determine the quality measure of the patient bracelet by determining the quality measure of the machine readable indicia printed on the patient bracelet. Determining the quality measure of the patient bracelet based on the quality measure of the machine readable indicia is described later in the flowchart 600.

In an example embodiment, the quality measure of the image is indicative of the quality of the patient bracelet (captured in the image). In yet another embodiment, the image processing unit 408 may be configured to determine the quality measure of a portion of the image. In such an embodiment, the image processing unit 408 may be configured to crop the image such that cropped image only includes the image of the patient bracelet. Thereafter, the image processing unit 408 may be configured to determine the quality measure of the cropped image by comparing the cropped image with an ideal image. In an alternate embodiment, the image processing unit 408 may be configured to determine the quality measure of the cropped image based on the quality measure of the machine readable indicia in the cropped image.

At step 508, the indicia scanner 102 may include means such as the second processor 402, the decoder unit 410, and/or the like for identifying the machine readable indicia in the image. In some examples, the decoder unit 410 may be configured to utilize one or more known edge detection techniques such as, but not limited to, canny edge detector, Laplacian edge detector, and/or the like to identify the one or more edges in the image. Thereafter, the decoder unit 410 may be configured to perform one or more morphological operations on the image (in which we have identified the one or more edges in the step 502). Some examples of the one or more morphological operations may include, but are not limited to, erosion, dilation, and/or the like, for isolating a portion of the image that includes the machine readable indicia. For example, after the morphological operations, the image may include a blob of white pixels. The blob of white pixels may indicate a location of the machine readable indicia in the image.

In some examples, the scope of the disclosure is not limited to identifying the machine readable indicia in the image using morphological operations. In some examples, the decoder unit 410 may be configured to utilize other methodologies to identify the first indicia in the image. For example, the decoder unit 410 may be configured to utilize one or more object identification algorithms (e.g., SIFT) to identify the machine readable indicia in the image.

At step 510, the indicia scanner 102 may include means such as the second processor 402, the decoder unit 410, and/or the like for decoding the machine readable indicia in the image to generate decoded data. In an example embodiment, the decoder unit 410 may be configured to decode the machine readable indicia using one or more known decoding algorithms. Prior to decoding the machine readable indicia, the decoder unit 410 may be configured to determine the barcode symbology identifier associated with the machine readable indicia. As discussed, the barcode symbology identifier may depict the type of the machine readable indicia. For example, the decoder unit 410 may be configured to identify known marking on the machine readable indicia to determine the type of the machine readable indicia in the image. In an example embodiment, the decoder unit 410 may be configured to utilize one or more known image processing techniques such edge detection, object identification, image binarization, and/or the like to identify known markings on the machine readable indicia.

For example, if the decoder unit 410 identifies one or more square patterns on the corners of the machine readable indicia, the decoder unit 410 may identify the type of the machine readable indicia as QR code. In another example, if the decoder unit 410 identifies a contiguous line on two orthogonal edges of the machine readable indicia, the decoder unit 410 may identify the type of the machine readable indicia as Datamatrix code. In yet another example, if the decoder unit 410 identifies multiple parallel lines in the machine readable indicia, the decoder unit 410 may be configured to identify the type of the machine readable indicia as Code 39. Thereafter, based on the known markings the decoder unit 410 may be configured to determine the barcode symbology identifier. Thereafter, the first decoder unit may be configured to utilize the one or more known decoding algorithms to decode the machine readable indicia based on the barcode symbology identifier.

At step 512, the indicia scanner 102 may include means such as the second processor 402, the decoder unit 410, and/or the like for determining whether decoding of the machine readable indicia is successful. If the decoding of the machine readable indicia is successful, the decoder unit 410 may be configured to perform the step 514. However, if the decoding of the machine readable indicia is unsuccessful, the decoder unit 410 may be configured to perform the step 518.

At step 514, the indicia scanner 102 may include means such as the second processor 402, the decoder unit 410, and/or the like for setting the decoding status as "success". Additionally or alternatively, at step 516, the indicia scanner 102 may include means such as the second processor 402, the decoder unit 410, and/or the like for generating the first set of patient characteristics that includes the decoded data. As discussed, the decoded data may include the name of the first patient, the age of the first patient, and the disease associated with the first patient.

At step 518, the indicia scanner 102 may include means such as the second processor 402, the decoder unit 410, and/or the like for setting the decoding status as "failed".

At step 520, the indicia scanner 102 may include means such as the second processor 402, the second communication interface 406, and/or the like for transmitting the first set of patient characteristics to the operator computing device 104. In an embodiment where the decode status is "fail", the second communication interface 406 may be configured to only transmit the decode status to the operator computing device 104 as the first set of patient characteristics. In alternate embodiment, the second communication interface 406 may be configured to transmit the first set of patient characteristics to the central server 108.

At step 522, the indicia scanner 102 may include means such as the second processor 402, the decoder unit 410, and/or the like for generating the one or more image characteristics. In an example embodiment, the one or more image characteristics comprise the decode status, and the quality measure of the image.

At step 524, the indicia scanner 102 may include means such as the second processor 402, the second communication interface 406, and/or the like for transmitting the one or more image characteristics to the central server 108.

Figure 6:
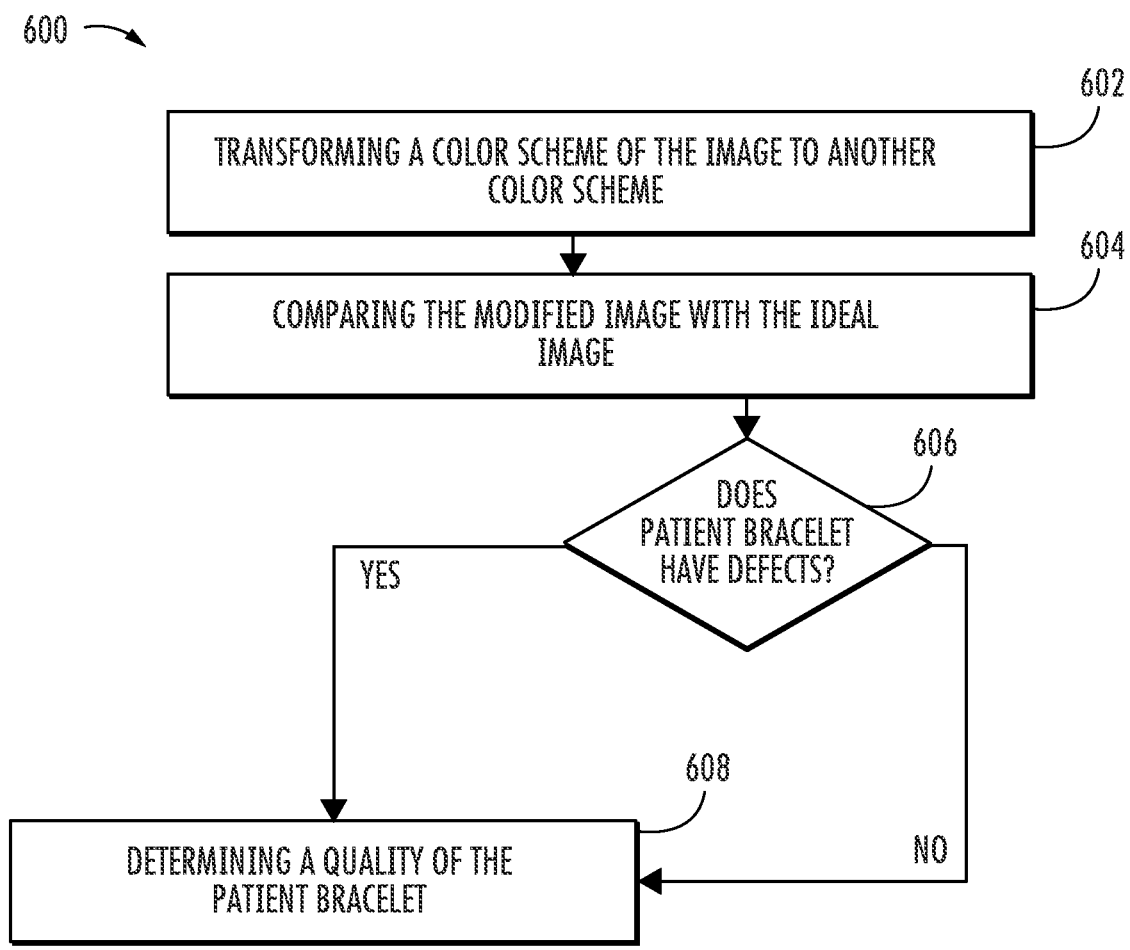
FIG. 6 illustrates a flowchart of a method for determining a quality measure of the image, according to one or more embodiments described herein.

FIG. 6 illustrates a flowchart 600 of a method for determining a quality measure of the image, according to one or more embodiments described herein.

At step 602, the indicia scanner 102 may include means such as the second processor 402, the image processing unit 410, and/or the like for transforming a color scheme of the image to another color scheme. The image in the other color scheme is hereinafter referred to as modified image. In an example embodiment, the image processing unit 410 may be configured to utilize known methodologies to transform the color scheme of the image. For example, the image processing unit 410 may be configured to convert the color scheme of the image to a 16 bit color scheme.

At step 604, the indicia scanner 102 may include means such as the second processor 402, the image processing unit 410, and/or the like for comparing the modified image with the ideal image. In an example embodiment, the ideal image may correspond to an image that includes an image of defect free object. For example, the ideal image may include an image of the patient bracelet that is devoid of any defects (i.e., smudges, and/or fading). In an example embodiment, the color scheme of the ideal image may be same as the color scheme of the modified image. In an example embodiment, the ideal image may be pre-stored in the indicia scanner 102 during manufacturing of the indicia scanner 102. In an alternate embodiment, the ideal image be retrieved from the central server 108. In such an embodiment, the central server 108 may be configured to store the ideal image, as is described later in conjunction with FIG. 8. For the purpose of ongoing description it is considered that the indicia scanner 102 is configured to retrieve the ideal image from the central server 108.

To compare the modified image with the ideal image, the image processing unit 410 may be configured to determine an intersection between the modified image and the ideal image. In an example embodiment, the intersection between the image and the ideal image facilitates highlighting common regions between the two images. Additionally, the intersection between the image and the ideal image identifies regions in the image that are dissimilar from the ideal image. Since the ideal image of the patient bracelet has no defects, therefore, intersection between the ideal image and the image may facilitate identification the regions on the patient bracelet that have faded away or have smudges based on the intersection between the image and the ideal image.

At step 606, the indicia scanner 102 may include means such as the second processor 402, the image processing unit 410, and/or the like for determining whether the patient bracelet has defects. In an example embodiment, if the image processing unit 410 determines that the patient bracelet has defects, the image processing unit 410 may be configured to perform the step 608. However, if the image processing unit 410 determines that the image is free from defects, the image processing unit 410 may be configured to perform the step 608.

At step 608, the indicia scanner 102 may include means such as the second processor 402, the image processing unit 410, and/or the like for determining a quality measure of the patient bracelet. In an example embodiment, the image processing unit 410 may be configured to determine a percentage of the of the patient bracelet (in the image) that includes the defects. For example, the image processing unit 410 may be configured to identify a count of pixels that represents the defects in the patient bracelet. Thereafter, the image processing unit 410 may be configured to determine a percentage of the total pixels (that represent the patient bracelet in the image) that has defects. In an example embodiment, the percentage of the total pixels that represent the defect in the image corresponds to the quality measure of the image.

In an embodiment, wherein the patient bracelet does not have any defects, the count of pixels that defects is zero. Accordingly, the quality measure of the patient bracelet is 100%.

In some examples, the scope of the disclosure is not limited to comparing the image with the ideal image to determine quality measure of the patient bracelet. In an example embodiment, the image processing unit 410 may be configured to consider a quality measure of the machine readable indicia (printed on the patient bracelet), as the quality measure of the patient bracelet. In such an embodiment, the image processing unit 410 may be configured to retrieve the machine readable indicia (printed on the patient bracelet) from the image, as identified in the step 508. Thereafter, the image processing unit 410 is configured to determine the quality measure of the machine readable indicia in accordance with one or more standards such as ANSI X3.182, ISO15415, and ISO/IEC 15416 standards.

Figure 7:
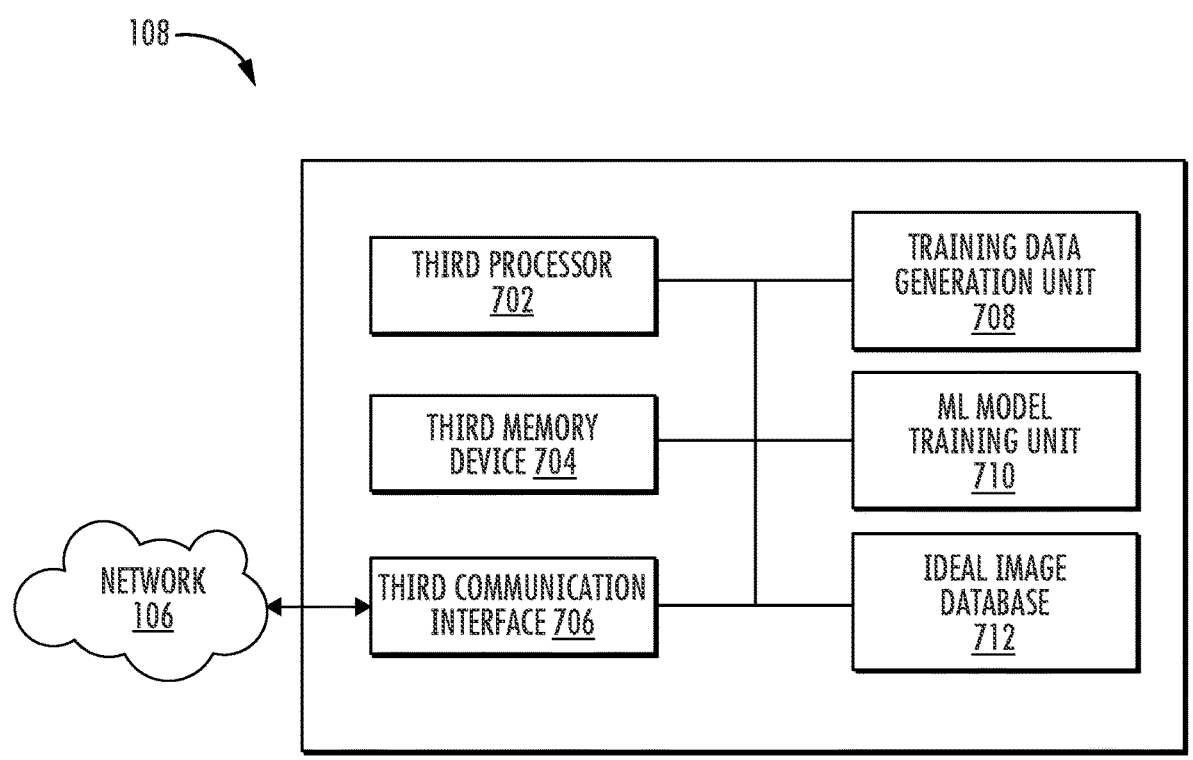
FIG. 7 illustrates a block diagram of a central server, according to one or more embodiments described herein.

FIG. 7 illustrates a block diagram of the central server 108, according to one or more embodiments described herein. In an example embodiment, the central server 108 includes a third processor 702, a third memory device 704, a third communication interface 706, a training data generation unit 708, a machine learning (ML) model training unit 710, and an ideal image database 712.

The third processor 702 may be embodied as a means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC) or field programmable gate array (FPGA), or some combination thereof. Accordingly, although illustrated in FIG. 7 as a single processor, in an embodiment, the third processor 702 may include a plurality of processors and signal processing modules. The plurality of processors may be embodied on a single electronic device or may be distributed across a plurality of electronic devices collectively configured to function as the circuitry of the central server 108. The plurality of processors may be in operative communication with each other and may be collectively configured to perform one or more functionalities of the circuitry of the indicia scanner 102, as described herein. In an example embodiment, the third processor 702 may be configured to execute instructions stored in the third memory device 704 or otherwise accessible to the third processor 702. These instructions, when executed by the third processor 702, may cause the circuitry of the central server 108 to perform one or more of the functionalities, as described herein.

Whether configured by hardware, firmware/software methods, or by a combination thereof, the third processor 702 may include an entity capable of performing operations according to embodiments of the present disclosure while configured accordingly. Thus, for example, when the third processor 702 is embodied as an ASIC, FPGA or the like, the third processor 702 may include specifically configured hardware for conducting one or more operations described herein. Alternatively, as another example, when the third processor 702 is embodied as an executor of instructions, such as may be stored in the first memory device 204, the instructions may specifically configure the third processor 702 to perform one or more algorithms and operations described herein.

Thus, the third processor 702 used herein may refer to a programmable microprocessor, microcomputer or multiple processor chip or chips that can be configured by software instructions (applications) to perform a variety of functions, including the functions of the various embodiments described above. In some devices, multiple processors may be provided dedicated to wireless communication functions and one processor dedicated to running other applications. Software applications may be stored in the internal memory before they are accessed and loaded into the processors. The processors may include internal memory sufficient to store the application software instructions. In many devices, the internal memory may be a volatile or nonvolatile memory, such as flash memory, or a mixture of both. The memory can also be located internal to another computing resource (e.g., enabling computer readable instructions to be downloaded over the Internet or another wired or wireless connection).

The third memory device 704 may include suitable logic, circuitry, and/or interfaces that are adapted to store a set of instructions that is executable by the third processor 702 to perform predetermined operations. Some of the commonly known memory implementations include, but are not limited to, a hard disk, random access memory, cache memory, read only memory (ROM), erasable programmable read-only memory (EPROM) & electrically erasable programmable read-only memory (EEPROM), flash memory, magnetic cassettes, magnetic tape, magnetic disk storage or other magnetic storage devices, a compact disc read only memory (CD-ROM), digital versatile disc read only memory (DVD-ROM), an optical disc, circuitry configured to store information, or some combination thereof. In an embodiment, the third memory device 704 may be integrated with the third processor 702 on a single chip, without departing from the scope of the disclosure.

The third communication interface 706 may correspond to a communication interface that may facilitate transmission and reception of messages and data to and from various devices operating in the system environment 100 through the network 106. For example, the third communication interface 706 is communicatively coupled with the indicia scanner 102 and the operator computing device 104, through the network 106. In some examples, through the third communication interface 706, the central server 108 may be configured to receive the one or more patient characteristics from the operator computing device 104. Additionally or alternately, through the third communication interface 706, the central server 108 may be configured to receive the one or more image characteristics from the indicia scanner 102. Examples of the third communication interface 706 may include, but are not limited to, an antenna, an Ethernet port, a USB port, a serial port, or any other port that can be adapted to receive and transmit data. The third communication interface 706 transmits and receives data and/or messages in accordance with the various communication protocols, such as but not limited to, I2C, TCP/IP, UDP, and 2G, 3G, 4G, or 5G communication protocols.

Figure 8:
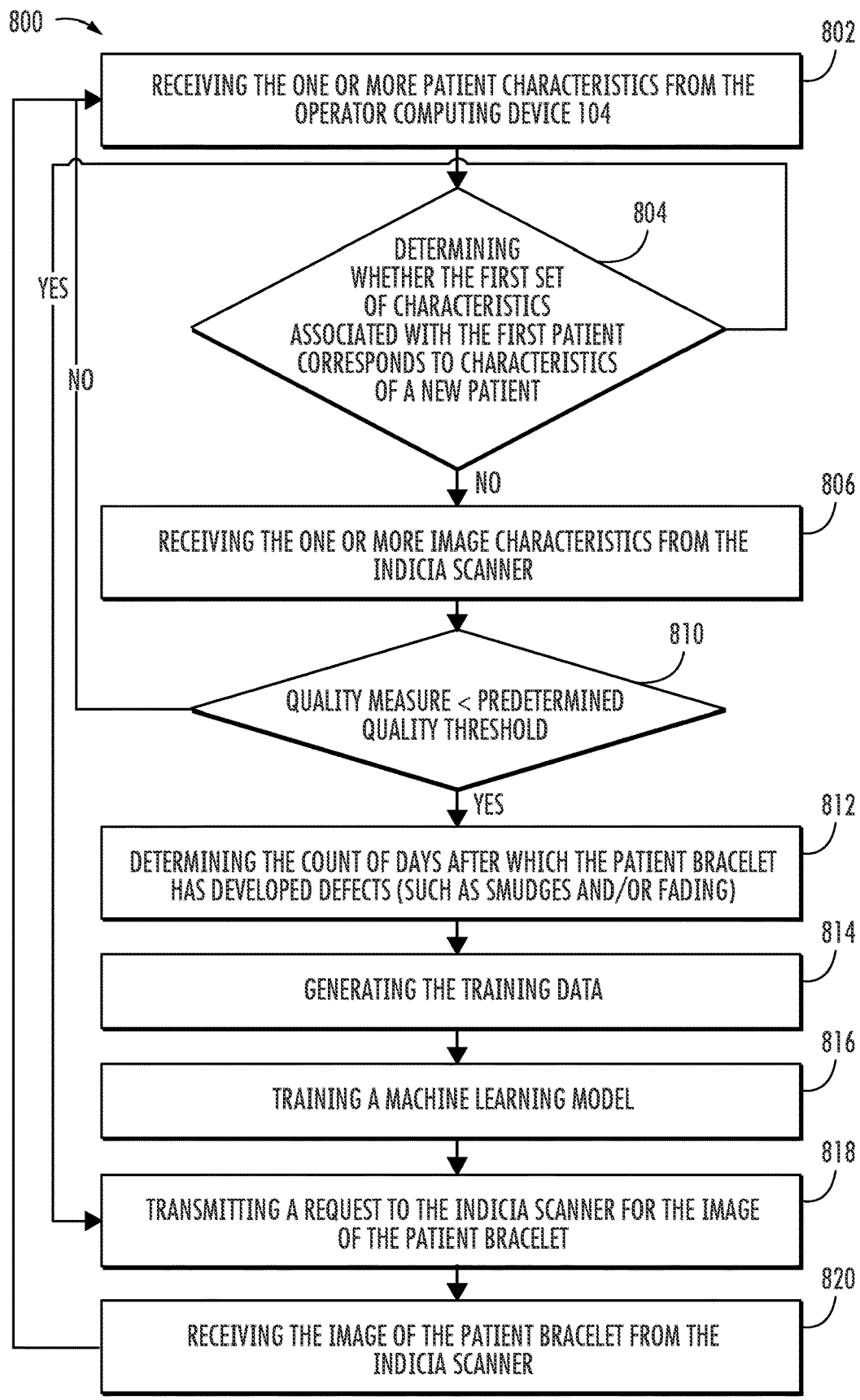
FIG. 8 illustrates a flowchart of a method for operating the central server, according to one or more embodiments described herein.

The training data generation unit 708 may include suitable logic and/or circuitry that may enable the central server 108 to generate the training data, as is described in FIG. 8. For example, the training data generation unit 708 may be configured to 'generate the training data based on the one or more patient characteristics and the one or more image characteristics, as is described in FIG. 8. In an example embodiment, the training data may include one or more features and one or more labels. The one or more features of the training data may include, but are not limited to, the first time period between successive scanning of the machine readable indicia, the current location of the patient within the hospital premises based on scanning of the machine readable indicia, a type of sanitizer historically used to disinfect the patient, a frequency of sanitizer usage, an age of the patient, the quality measure of the patient bracelet (received from indicia scanner), the decode status, and/or a disease associated with the patient. The one or more labels of the training data may include, but are not limited to, the count of days after which the patient bracelet had defects.

In some examples, the training data generation unit 708 may be configured to determine the one or more features and the one or more labels of the training data, as is described in FIG. 8. For example, the training data generation unit 708 determine a first time period between successive scanning of the machine readable indicia (printed on the patient bracelet), as is described in FIG. 8. Further, the central server 108 may be configured to determine a count of days until the patient bracelet was printed, as is described in FIG. 8. The training data generation unit 708 may be implemented using one or more of Application Specific Integrated Circuit (ASIC) and Field Programmable Gate Array (FPGA).

The ML model training unit 710 may include suitable logic and/or circuitry that enables the central server to train a ML model based on the training data, as is described in FIG. 8. In an example embodiment, the ML model training unit 710 may be configured to utilize one or more known machine learning techniques such as, but not limited to, a logistic regression, K-means clustering, centroid clustering, naïve Bayes, neural networks, Gaussian Copula, and/or the like to train the ML model. In an example embodiment, the ML model may define a mathematical relation between the one or more features and the one or more labels in the training data. The ML model training unit 710 may be implemented using one or more of Application Specific Integrated Circuit (ASIC) and Field Programmable Gate Array (FPGA).

In an example embodiment, the ideal image database 712 may correspond to a repository of the one or more ideal images of one or more patient bracelets worn by one or more patients admitted in the hospital. In an example embodiment, the third processor 702 may be configured to update the ideal image database 712 with new images, as is described in conjunction with FIG. 8. Some examples of the ideal image database 712 may include, but not limited to, SQL database, mongo DB, and/or the like.

FIG. 8 illustrates a flowchart 800 of a method for operating the central server 108, according to one or more embodiments described herein.

At step 802, the central server 108 may include means such as the third processor 702, the third communication interface 706, and/or the like for receiving the one or more patient characteristics (associated with the first patient) from the operator computing device 104.

At step 804, the central server 108 may include means such as the third processor 702, the training data generation unit 708, and/or the like for determining whether the first set of characteristics associated with the first patient corresponds to characteristics of a new patient. In an example embodiment, the training data generation unit 708 may be configured to compare the first set of patient characteristics with the previously received first set of patient characteristics associated with other patients. If the first set of patient characteristics matches with one of the previously received first set of patient characteristics, the training data generation unit 708 may be configured to determine that the first set of patient characteristics associated with the first patient does not correspond to a new patient. Accordingly, the training data generation unit 708 may be configured to perform the step 806. However, if the training data generation unit 708 determines that the first set of patient characteristics correspond to new patient, the training data generation unit 708 may be configured to perform the step 818.

At step 806, the central server 108 may include means such as the third processor 702, the training data generation unit 708, and/or the like for receiving the one or more image characteristics from the indicia scanner 102. In some examples, prior to receiving the one or more image characteristics associated with the image captured by the indicia scanner 102, the training data generation unit 708 may be configured to receive a request to access the ideal image. Upon receiving the request, the training data generation unit 708 may be configured to retrieve the ideal image associated with the patient bracelet worn by the first patient from the ideal image database 712. Further, the training data generation unit 708 may be configured to transmit the ideal image to the indicia scanner 102. Thereafter, the training data generation unit 708 receives the one or more image characteristics associated with the image of the patient bracelet worn by the first patient.

At step 810, the central server 108 may include means such as the third processor 702, the training data generation unit 708, and/or the like for determining whether the quality measure of the patient bracelet (received in the one or more image characteristics) is less than a predetermined quality threshold. In an example embodiment, the predetermined quality threshold may correspond to a quality measure below which the machine readable indicia printed on the patient bracelet is not readable and/or not decodable. If the training data generation unit 708 determines that the quality measure of the patient bracelet is less than the predetermined quality threshold, the training data generation unit may be configured to perform the step 812. However, if the training data generation unit 708 determines that the quality measure is greater than the predetermined quality threshold, the training data generation unit 708 may be configured to repeat the step 802.

In some examples, the predetermined quality threshold may correspond to a percentage of defective pixels in an image above which the barcode in the image is unreadable. In some examples, the predetermined quality threshold is pre-stored in the central server 108. In an alternate embodiment, the training data generation unit 708 may determine the predetermined quality threshold based on the historical data (i.e., the data received prior to receiving the one or more patient characteristics). For example, the training data generation unit 708 may determine a percentage of defected pixels in the image of the patient bracelet (in the historical data), where decoding of the barcode is unsuccessful. Thereafter, the training data generation unit 708 may determine a minimum of the percentage of defected pixels amongst the historical data, as the predetermined quality threshold. For example, the training data generation unit 708 may determine that when 10% of image pixels are defective, the decoding of the barcode fails. Accordingly, the training data generation unit 708 may determine 10% as the predetermined quality threshold.

In some examples, the scope of the disclosure is not limited to performing the step 810 to determine whether the quality of the patient bracelet has degraded. In an example embodiment, the training data generation unit 708 may be configured to determine the quality of the patient bracelet based on the decode status received in the one or more image characteristics associated with the image of the patient bracelet. If the decode status is "fail", the training data generation unit 708 may be configured to determine that the quality of the patient bracelet has degraded. However, if the decode status is "success", the training data generation unit 708 may be configured to determine that the quality of the patient bracelet has not degraded.

At step 812, the central server 108 may include means such as the third processor 702, the training data generation unit 708, and/or the like for determining the count of days after which the patient bracelet has developed defects (such as smudges and/or fading). In an example embodiment, the training data generation unit 708 may be configured to determine a difference between the first time stamp, at which the training data generation unit 708 received the one or more patient characteristics associated with the first patient for the first time, and a second time stamp at which the training data generation unit 708 last received the one or more patient characteristics associated with the first patient. In an example embodiment, the difference between the first time stamp and the second time stamp corresponds to the count of days after which the patient bracelet has developed defects.

At step 814, the central server 108 may include means such as the third processor 702, the training data generation unit 708, and/or the like for generating the training data. In an example embodiment, the training data generation unit 708 may be configured to define the one or more features and the one or more labels of the training data. In some examples, the training data generation unit 708 may be configured to determine the count of days after which the patient bracelet has developed defects as the one or more label. Further, the training data generation unit 708 may be configured to determine the current location of the patient (retrieved from the one or more patient characteristics), a type of sanitizer historically used to disinfect the patient (retrieved from the one or more patient characteristics), a frequency of sanitizer usage (retrieved from the one or more patient characteristics), an age of the patient (retrieved from the one or more patient characteristics), the quality measure of the patient bracelet (retrieved from the one or more image characteristics), the decode status (retrieved from the one or more patient characteristics), and/or a disease associated with the patient (retrieved from the one or more patient characteristics), as the one or more features of the training data.

At step 816, the central server 108 may include means such as the third processor 702, the ML model training unit 710, and/or the like for training a machine learning model. In an example embodiment, the ML model training unit 710 may be configured to utilize one or more machine learning techniques such as but not limited to, the logistic regression, the K-means clustering, the centroid clustering, the naïve Bayes, neural networks, Gaussian Copula, and/or the like to train the ML model. For example, the ML model training unit 710 may be configured to determine one or more clusters in the training data using the Elbow method. In an example embodiment, the one or more clusters may define one or more relations between the one or more features and the one or more labels. For example, the ML model training unit may define a cluster that defines relation between the age of the first patient and the count of days after which the patient bracelet has developed defects. Similarly, the ML model training unit 710 may be configured to define other clusters in the training data. thereafter, the ML model training unit may be configured to determine a centroid for each cluster. In an example embodiment, the one or more clusters and the corresponding centroid may correspond to the trained ML model. In an example embodiment, the ML model training unit 710 may be configured to store the ML model in the third memory device 704.

At step 818, the central server 108 may include means such as the third processor 702, the training data generation unit 708, and/or the like for transmitting a request to the indicia scanner 102 for the image of the patient bracelet. At step 820, the central server 108 may include means such as the third processor 702, the training data generation unit 708, and/or the like for receiving the image of the patient bracelet from the indicia scanner 102. In some examples, the training data generation unit 708 may be configured to store the image of the patient bracelet as the ideal image of the patient bracelet (associated with the first patient) in the ideal image database 712. Thereafter, the third processor 702 may be configured to repeat the step 802.

In some examples, the scope of the disclosure is not limited to the central server 108 performing the steps 818 and 820. In an alternate embodiment, the central server 108 is request transmit a request to the operator computing device 104 to retrieve the one or more patient characteristics. Thereafter, the central server 108 may be configured to generate an image that was utilized to print the patient bracelet based on the one or more patient characteristics. The image is considered as the ideal image of the patient bracelet. For example, the central server 108 may be configured to generate an image of a barcode based on the first set of patient characteristics. In the example, the image of the barcode is considered as the ideal image.

Figure 9:
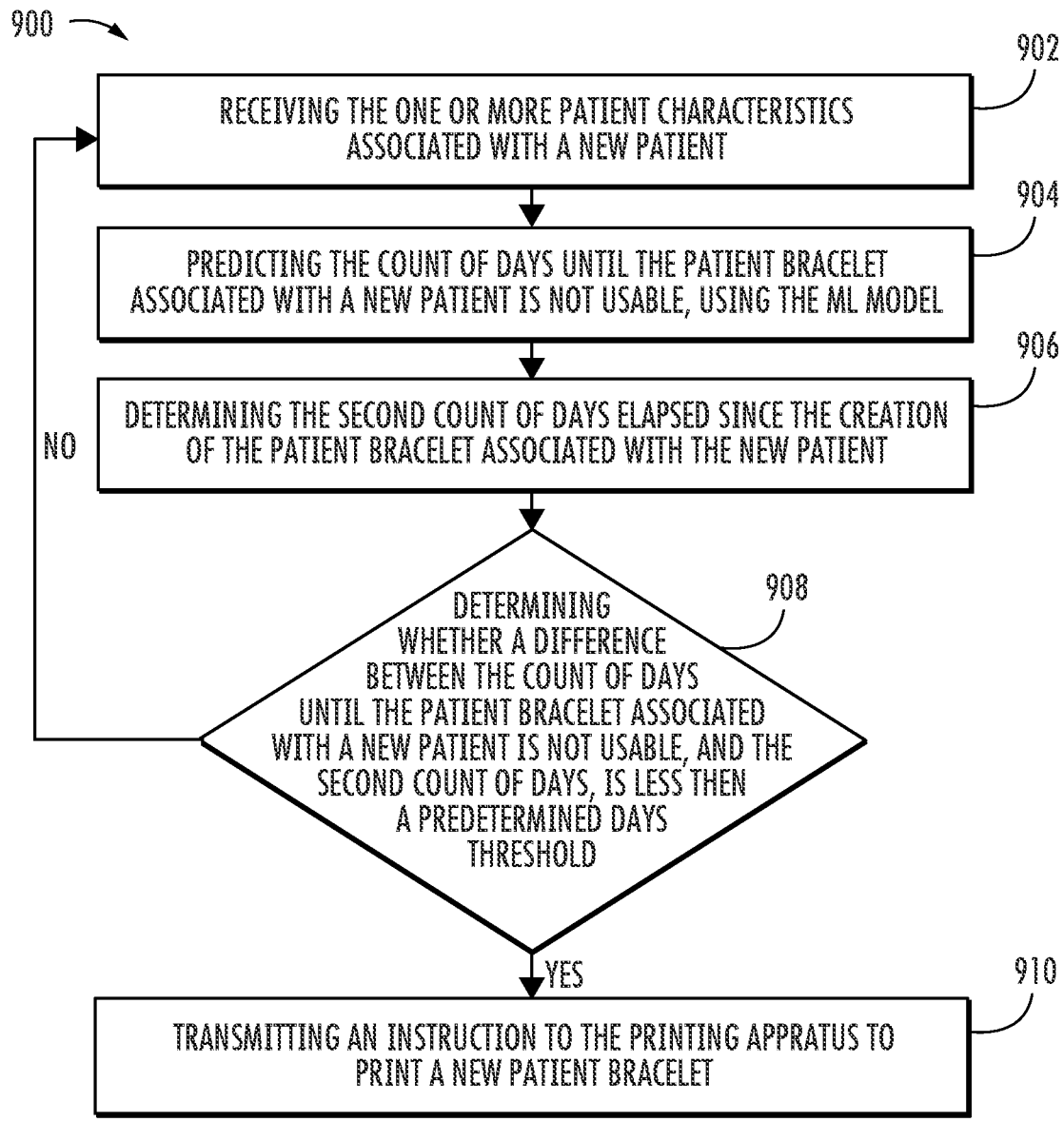
FIG. 9 illustrates a flowchart of a method for predicting a count of days until the patient bracelet associated with a new patient is not usable, according to one or more embodiments described herein.

FIG. 9 illustrates a flowchart 900 of a method for predicting a count of days until the patient bracelet associated with a new patient is not usable, according to one or more embodiments described herein.

At step 902, the central server 108 may include means such as the third processor 702 and/or the like for receiving the one or more patient characteristics associated with a new patient. In an example embodiment, the third processor 702 may receive, the one or more patient characteristics associated with a new patient, from the operator computing device 104.

At step 904, central server 108 may include means such as the third processor 702 and/or the like for predicting the count of days until the patient bracelet associated with a new patient is not usable, using the ML model trained on in the step 816.

At step 906, central server 108 may include means such as the third processor 702 and/or the like for determining the second count of days elapsed since the creation of the patient bracelet associated with the new patient. In an example embodiment, the third processor 702 may be configured to utilize the methodologies described in the step 812 to determine the second count of days elapsed since the creation of the patient bracelet.

At step 908, central server 108 may include means such as the third processor 702 and/or the like for determining whether a difference between the count of days until the patient bracelet associated with a new patient is not usable, and the second count of days, is less than a predetermined days threshold. If the third processor 702 determines that the difference is less than the predetermined days threshold, the third processor 702 may be configured to perform the step 910. However, if the third processor 702 determines that the difference is greater than the predetermined days threshold, the third processor 702 may be configured to repeat the step 902. In some examples, the predetermined day threshold is less than the count of days until the patient bracelet associated with a new patient is not usable. Further, in some examples, the predetermined threshold is defined during configuration of the software. In an alternate embodiment, the predetermined threshold is configurable and may be defined in real time (i.e., during execution of the flowchart 800).

At step 910, central server 108 may include means such as the third processor 702 and/or the like for transmitting an instruction to the printing apparatus 110 to print a new patient bracelet. Since the predetermined day threshold is less than the count of days until the patient bracelet associated with a new patient is not usable, the central server 108 may print a new patient bracelet prior to the patient bracelet becoming unreadable.

In some examples, the scope of the disclosure is not limited to having three separate computing devices (indicia scanner 102, the operator computing device 104, and the central server 108) to perform the aforementioned operation. In an example embodiment, the system environment 100 may include only one computing device that is capable of performing the operations of the indicia scanner 102, the operator computing device 104, and the central server 108

In an example embodiment, the scope of the disclosure is not limited to predicting the life of the patient bracelet in the hospital environment. The disclosed embodiment may be applicable on any printed label utilized any domain. For example, disclosed systems and methods may be utilized to predict the printed label in logistic environment. In such an embodiment, instead of the one or more patient characteristics, the attendant may utilize operator computing device 104 for transmitting one or more object characteristics. In an example embodiment, the one or more object characteristics may include, but not limited to, a destination of the object, a traversal history of the object, a storage temperature of the object, a type of sanitization used to disinfect the object, and/or a frequency of sanitization. In an example embodiment, the central server 108 upon receiving the one or more object characteristics, the central server 108 may be configured to train the ML model the one or more object characteristics and the one or more image characteristics. Thereafter, the central server 108 may be configured to utilize the ML model to predict the life of the printed label attached on new object based on the one or more object characteristics associated with the new object.

For example, in a shipping warehouse, the operator computing device 104 may input the one or more object characteristics that may include a number of times an object was handled by an operator, a number of times the object of sanitized, the traversal history of the object, storage temperature of the object, a type of sanitization used to disinfect the object, and/or a frequency of sanitization. For example, the operator of the operator computing device 104 may input that an object was sanitized every 5 hours, the object was handled by 10 different workers in the warehouse, the object was previously handled at 5 different locations, and/or the like. Thereafter, the central server 108 may be configured to train the ML model the one or more object characteristics and the one or more image characteristics. Thereafter, the central server 108 may be configured to utilize the ML model to predict the life of the printed label attached on new object based on the one or more object characteristics associated with the new object.

In the specification and figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing detailed description has set forth various embodiments of the devices and/or processes via the use of block diagrams, flow charts, schematics, exemplary, and examples. Insofar as such block diagrams, flow charts, schematics, and examples contain one or more functions and/or operations, each function and/or operation within such block diagrams, flowcharts, schematics, or examples can be implemented, individually and/or collectively, by a wide range of hardware thereof.

In one embodiment, examples of the present disclosure may be implemented via Application Specific Integrated Circuits (ASICs). However, the embodiments disclosed herein, in whole or in part, can be equivalently implemented in standard integrated circuits, as one or more computer programs running on one or more computers (e.g., as one or more programs running on one or more computer systems), as one or more programs running on one or more processing circuitries (e.g., micro-processing circuitries), as one or more programs running on one or more processors (e.g., microprocessors), as firmware, or as virtually any combination thereof.

In addition, those skilled in the art will appreciate that example mechanisms disclosed herein may be capable of being distributed as a program product in a variety of tangible forms, and that an illustrative embodiment applies equally regardless of the particular type of tangible instruction bearing media used to actually carry out the distribution. Examples of tangible instruction bearing media include, but are not limited to, the following: recordable type media such as floppy disks, hard disk drives, CD ROMs, digital tape, flash drives, and computer memory.

The various embodiments described above can be combined with one another to provide further embodiments. For example, two or more of example embodiments described above may be combined to, for example, improve the safety of laser printing and reduce the risks associated with laser-related accidents and injuries. These and other changes may be made to the present systems and methods in light of the above detailed description. Accordingly, the disclosure is not limited by the disclosure, but instead its scope is to be determined by the following claims.

What is claimed is:

1. A method comprising:
receiving, by a processor, one or more patient characteristics associated with a first patient, wherein the one or more patient characteristics comprises at least a type of sanitization, and/or a frequency of sanitization usage;
receiving, by the processor, one or more image characteristics associated with an image of a patient bracelet worn by the first patient; and training, by the processor, a machine learning (ML) model defining a relation between the one or more patient characteristics and the one or more image characteristics, wherein the ML model is utilized to predict a count of days until the patient bracelet, associated with a second patient, deems unusable; and generating, by the processor, an instruction to a printing apparatus to print a new patient bracelet for the second patient based on the count of days being less than a predetermined number of days threshold.

2. The method of claim 1, wherein the one or more image characteristics comprises a quality measure of the patient bracelet in the image.

3. The method of claim 2 further comprising comparing, by the processor, whether the quality measure of the patient bracelet in the image is less than a predetermined quality threshold, wherein the predetermined quality threshold a percentage of defective pixels in the image.

4. The method of claim 3 further comprising determining, by the processor, a count of days elapsed since printing of the patient bracelet, in response to determining that the quality measure of the patient bracelet is less than the predetermined quality threshold.

5. The method of claim 1, wherein the one or more image characteristics comprises a decode status of a machine readable indicia printed on the patient bracelet, wherein the decode status is indicative of a quality measure of the patient bracelet in the image, wherein the quality measure comprises a percentage of defective pixels in the image.

6. The method of claim 1, generating training data based on the one or more patient characteristics associated with the first patient and the one or more image characteristics, wherein the training data comprises one or more features and one or more labels, wherein the one or more features comprises a current location of the first patient, the type of sanitization used to disinfect the first patient, the frequency of sanitizer usage, an age of the first patient, a quality measure of the patient bracelet, a decode status of a machine readable indicia printed on patient bracelet, and/or a disease associated with the first patient.

7. The method of claim 1 further comprising receiving, by the processor, the one or more patient characteristics associated with the second patient, wherein the ML model predicts the count of days based on the one or more patient characteristics associated with the second patient.

8. The method of claim 1 further comprising determining, by the processor, whether the one or more patient characteristics associated with the first patient corresponds to patient characteristics of a new patient.

9. The method of claim 8 further comprising in response to determining that the first patient corresponds to a new patient, transmitting, by the processor, an instruction to an indicia scanner to transmit the image of the patient bracelet.

10. The method of claim 9 further comprising storing, by the processor, the image of the patient bracelet as an ideal image for patient bracelet worn by the first patient.

11. A central server comprising:
a memory device storing one or more instructions; and
a processor communicatively coupled to the memory device, wherein the processor is configured to:
receive one or more patient characteristics associated with a first patient, wherein the one or more patient characteristics comprises at least a type of sanitization, and/or a frequency of sanitization usage,
receive one or more image characteristics associated with an image of a patient bracelet worn by the first patient,
train a machine learning (ML) model defining a relation between the one or more patient characteristics and the one or more image characteristics, wherein the ML model is utilized to predict a count of days until the patient bracelet, associated with a second patient, deems unusable, and
generate an instruction to a printing apparatus to print a new patient bracelet for the second patient based on the count of days being less than a predetermined days threshold.

12. The central server of claim 11, wherein the one or more image characteristics comprises a quality measure of the patient bracelet in the image.

13. The central server of claim 12, wherein the processor is further configured to compare whether the quality measure of the patient bracelet in the image is less than a predetermined quality threshold, wherein the predetermined quality threshold a percentage of defective pixels in the image.

14. The central server of claim 13, wherein the processor is further configured to determine a count of days elapsed since printing of the patient bracelet, in response to determining that the quality measure of the patient bracelet is less than the predetermined quality threshold.

15. The central server of claim 11, wherein the one or more image characteristics comprises a decode status of a machine readable indicia printed on the patient bracelet, wherein the decode stains is indicative of a quality measure of the patient bracelet in the image, wherein the quality measure comprises a percentage of defective pixels in the image.

16. The central server of claim 11, wherein the processor is further configured to generate training data based on the one or more patient characteristics associated with the first patient and the one or more image characteristics, wherein the training data comprises one or more features and one or more labels, wherein the one or more features comprises a current location of the first patient, the type of sanitization used to disinfect the first patient, the frequency of sanitizer usage, an age of the first patient, a quality measure of the patient bracelet, a decode status of a machine readable indicia printed on patient bracelet, and/or a disease associated with the first patient.

17. The central server of claim 11, wherein the processor is further configured to receive the one or more patient characteristics associated with the second patient, wherein the ML model predicts the count of days based on the one or more patient characteristics associated with the second patient.

18. The central server of claim 11, wherein the processor is further configured to determine whether the one or more patient characteristics associated with the first patient corresponds to patient characteristics of a new patient.

19. The central server of claim 18, wherein in response to determining that the first patient corresponds to a new patient, the processor is further configured to transmit an instruction to an indicia scanner to transmit the image of the patient bracelet.

20. The central server of claim 19, wherein the processor is configured to store the image of the patient bracelet as an ideal image for patient bracelet worn by the first patient.

* * * * *